(12) United States Patent
Wimmer et al.

(10) Patent No.: US 6,365,541 B1
(45) Date of Patent: Apr. 2, 2002

(54) ALKOXYLATION CATALYST

(75) Inventors: Ignaz Wimmer, Winhöring; Hildegard Freundl, Burgkirchen, both of (DE)

(73) Assignee: Clariant GmbH, Frankfurt (DE)

( * ) Notice: Subject to any disclaimer, the term of this patent is extended or adjusted under 35 U.S.C. 154(b) by 0 days.

(21) Appl. No.: 09/257,630

(22) Filed: Feb. 25, 1999

(30) Foreign Application Priority Data

Feb. 26, 1998 (DE) .......................................... 198 07 991

(51) Int. Cl.⁷ .......................... B01J 31/00; C07C 69/66; C07C 43/18; C07C 39/24
(52) U.S. Cl. ...................... 502/170; 560/180; 560/182; 568/618; 568/619; 568/678; 568/679; 568/680
(58) Field of Search .......................... 502/170; 568/618, 568/619, 678–680; 560/180, 182

(56) References Cited

U.S. PATENT DOCUMENTS

| | | | |
|---|---|---|---|
| 4,820,673 A | * | 4/1989 | Knopf et al. |
| 4,996,364 A | | 2/1991 | Behler et al. |
| 5,600,020 A | | 2/1997 | Wehle et al. |
| 5,840,995 A | | 11/1998 | Mayer et al. |

FOREIGN PATENT DOCUMENTS

| | | | |
|---|---|---|---|
| DE | 4225136 | | 2/1994 |
| DE | 19546946 | * | 6/1997 |
| EP | 0337239 | | 10/1989 |
| EP | 0657410 | | 6/1995 |
| EP | 0779101 | | 6/1997 |
| GB | 796508 | * | 8/1955 |

OTHER PUBLICATIONS

EPO Search Report.
Derwent Patent Family Report and/or Abstract.

* cited by examiner

*Primary Examiner*—Gary Geist
*Assistant Examiner*—Leigh C. Maier
(74) *Attorney, Agent, or Firm*—Susan S. Jackson; Scott E. Hanf

(57) ABSTRACT

An alkoxylation catalyst is prepared by a) reaction of one mol of a dicarboxylic acid with from 1.5 to 8 mol of an alkoxylated alcohol to form the corresponding dicarboxylic monoester, b) formation of an alkaline earth metal salt of the dicarboxylic monoester by addition of water and from 0.45 to 0.55 mol of a basic alkaline earth metal compound per mol of dicarboxylic acid originally used, c) partial neutralization of the alkaline earth metal salt by addition of from 0.25 to 0.7 mol of $H_2SO_4$ per mol of basic alkaline earth metal compound originally used and d) removal of the water present at a temperature of less than 100° C.

The catalyst prepared in this way makes it possible to prepare colorless alkoxylates having a narrow homologue distribution.

2 Claims, No Drawings

ALKOXYLATION CATALYST

BACKGROUND OF THE INVENTION

EP-A-337 239 has already disclosed the use of alkaline earth metal salts of monoesters of dicarboxylic acids and alkoxylated alcohols as catalysts for preparing narrow range alkoxylates. EP-A-657 410 describes the use of alkaline earth metal salts of monoesters of alkylsuccinic or alkenylsuccinic acid and alkoxylated alcohols for the same purpose. In both cases, the unesterified carboxyl group is completely converted into the form of the alkaline earth metal salt. It has now been found that the effectiveness of this type of catalyst can be further improved if the carboxylate group is only partially converted into the salt form.

Such partially neutralized Ca salts of succinic monoesters and their use as alkoxylation catalysts have already been described in U.S. Pat. No. 5,600,020. However, these succinic monoesters are substituted by a $C_8$–$C_{30}$-alkyl radical. Alkoxylation catalysts of the above-described type based on alkylsuccinic monoesters are, however, obtained as colored products and give colored alkoxylation products. In contrast, the alkoxylation catalysts described below give largely colorless alkoxylation products having a narrow homologue distribution.

SUMMARY OF THE INVENTION

The invention provides an alkoxylation catalyst which is prepared by a) reaction of one mol of a dicarboxylic acid of the formula

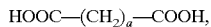
$$HOOC—(CH_2)_a—COOH,$$

where a is from 1 to 4, with from 1.5 to 8 mol of an alcohol of the formula

$$R—(OA)_x—OH$$

where R is $C_4$–$C_{22}$-alkyl, $C_4$–$C_{22}$-alkenyl or a group of the formula $F—(CF_2)_n—(CH_2)_m—$, n is an integer from 6 to 16, m is an integer from 1 to 4, x is from 0 to 6 and A is —$C_2H_4$— or —$C_3H_6$—, to form the corresponding dicarboxylic monoester, b) formation of an alkaline earth metal salt of the dicarboxylic monoester by addition of water and from 0.45 to 0.55 mol of a basic alkaline earth metal compound per mol of dicarboxylic acid originally used, c) partial neutralization of the alkaline earth metal salt by addition of from 0.25 to 0.7 mol of $H_2SO_4$ per mol of basic alkaline earth metal compound originally used and d) removal of the water present at a temperature of less than 100° C.

DESCRIPTION OF THE PREFERRED EMBODIMENTS

The dicarboxylic monoester is prepared by methods known per se, as described, for example, in U.S. Pat No. 5,600,020. The reaction is generally carried out at from 70 to 140°, preferably from 80 to 110° C. The molar ratio of alcohol to dicarboxylic acid is from about 1.5:1 to 8:1, preferably from 3:1 to 6:1. Naturally, the corresponding acid anhydride can also be used as starting material in place of the dicarboxylic acid. Preference is given to succinic anhydride. In the case of alcohols of the formula R—(OA)$_x$—OH, A is preferably —$C_2H_4$—.

In the second reaction step, the acidic monoester is converted into an alkaline earth metal salt by addition of a basic alkaline earth metal compound, preferably an oxide, carbonate or hydroxide of barium, strontium, in particular calcium. The amount of basic alkaline earth metal compound is from about 0.45 to 0.55 mol, preferably 0.5 mol, per mol of the acidic monoester or per mol of dicarboxylic acid or dicarboxylic anhydride. Water is added to aid salt formation. The amount of water is not critical but, for practical reasons, an amount of water which is equal to the amount of basic alkaline earth metal compound or is up to three times that is generally employed. Higher amounts of water bring no advantage and merely increase the amount of water which has to be removed again in the final step. To complete salt formation, the mixture is generally stirred for a plurality of hours at from 60 to 100° C., preferably from 80 to 95° C.

The partial neutralization is carried out by addition of $H_2SO_4$ in the amount indicated at from 20 to 80° C., preferably from 40 to 70° C. Preference is given to using from 0.3 to 0.6 mol of $H_2SO_4$ per mol of basic alkaline earth metal compound originally used.

In the final step, the water present is distilled off under reduced pressure, during which the temperature should not exceed 100° C. The water is preferably removed under reduced pressure for from 1 to 5 hours at from 50 to 100° C., preferably from 70 to 90° C. This gives the alkoxylation catalyst in the form of a white, more or less viscous slurry containing the unreacted excess of the alcohol of the formula R—(OA)$_x$—OH. This slurry can be used directly as catalyst in alkoxylation reactions.

The alkoxylation, i.e. the reaction of compounds containing active H atoms with alkylene oxides using the products according to the invention as catalyst, is carried out in a customary manner, i.e. at a temperature of from 60 to 200° C., preferably from 100 to 180° C., and a pressure of from about 0.5 to 6 bar, with the alkylene oxide being metered in a little at a time or continuously. The amount of alkylene oxide is generally from 1 to 30 mol, preferably from 2 to 20 mol and in particular from 2 to 15 mol, per mol of compound to be alkoxylated. The alkoxylate obtained can generally be used without prior removal of the catalyst.

According to one variant, the catalyst can be generated in situ. This is done by adding the alkaline earth metal salt produced in step b) to the compound which is to be alkoxylated and then carrying out steps c) and d) in the presence of this compound.

The amount of catalyst of the invention can vary within wide limits and is generally from 0.1 to 5% by weight, preferably from 0.5 to 3% by weight, based on the weight of the compound to be alkoxylated.

Compounds which can be alkoxylated with the aid of the catalyst of the invention are all compounds having an active H atom. Even compounds without an active H atom, e.g. alkyl esters of fatty acids, can be alkoxylated using the catalyst of the invention (insertion of ethylene oxide into the ester group).

Compounds containing active H atoms are, for example, hydroxyl-containing compounds, amine compounds and acid compounds such as fatty acids, with preference being given to the former. Examples of hydroxyl-containing compounds are alcohols, aminoalcohols, perfluoroalkyl alcohols, glycols, glycol monoethers, glycerol, phenols, cresols, and the like, with preference being given to alcohols. They can originate from natural sources or from synthetic processes and be primary, linear or branched, saturated or unsaturated, monohydric or polyhydric, for example, oxo alcohols, Guerbet alcohols, Ziegler alcohols, fatty alcohols, fluoroalcohols and the like. Preferred alcohols are primary, straight-chain or branched $C_3$–$C_{24}$-alkanols, preferably $C_6$–$C_{18}$-alkanols (fatty alcohols) or mixtures thereof, for example mixtures of $C_{12}$- and $C_{14}$-alkanol ($C_{12/14}$), and also perfluorinated alcohols. Examples of preferred alcohols are: butanol, amyl alcohol, hexanol, nonanol, isononyl alcohol, decanol, undecanol, isoundecanol, lauryl alcohol, isotridecyl alcohol, stearyl alcohol, coconut fatty alcohol and mixtures thereof, also 2-ethylhexanol, 2-hexyldecanol, 2-octyldecanol and similar Guerbet alcohols.

As alkylene oxides, preference is given to using ethylene oxide, propylene oxide and/or butylene oxide, with ethylene oxide being preferred.

The alkoxylation catalyst prepared according to the invention has a high catalytic activity and, in a relatively short reaction time, leads to virtually complete conversion and to a high yield. The alkoxylate has a narrow homologue distribution and is colorless and frequently clear and thus has a good appearance.

In particular, the ethyoxylation of alkyl esters of fatty acids gives, due to the narrow homologue distribution and the high degree of conversion, more uniform products and less by-products compared to conventional catalysis using basic Na or K compounds.

EXAMPLE A1

Step 1 (Ester Formation)

582 g (=3.00 mol) of $C_{12}/C_{14}$-alcohol were weighed into a heatable stirred vessel. After heating to about 60° C., 100 g (=1.00 mol) of succinic anhydride flakes (SA) were added over a period of about 15 minutes while stirring. Subsequently, the mixture was heated to 100° C. over ½ hour. A slightly exothermic reaction occurred and the reaction mixture heated up to about 110° C.

Stirring was continued for 1 hour at 90° C. and the acid number was subsequently checked (sample dissolved in IPA/water, potentiometric titration with NaOH). An acid number of 80 [mg KOH/g] was found.

Step 2 (Ca Salt Formation)

37.0 g of calcium hydroxide powder (=0.50 mol of $Ca(OH)_2$) together with the same amount of water were added at 80° C. over a period of 20–30 minutes. A slightly exothermic reaction could be detected. Stirring was subsequently continued for 2 hours at 90–95° C. to ensure complete Ca salt formation. This gave a white suspension which had a medium viscosity at 25° C. The alkali number is determined by potentiometric titration with $HClO_4$ in glacial acetic acid. An alkali number of 75 [mg KOH/g] was found. This slurry is a precursor of the catalyst system of the invention, whose activity is not yet sufficient for industrial use.

Step 3 (Partial Neutralization)

49 g of 40% strength sulfuric acid were added at 60° C. to the basic $C_{12}/C_{14}$-alcohol monoester of succinic acid from step 2 while stirring. This amount corresponds to 40% neutralization of the Ca basicity present.

Step 4 (Drying)

The partially neutralized product was heated to from 75 to a maximum of 80° C. and the water present was removed under reduced pressure.

EXAMPLE A2

Step 1 (Ester Formation)

291 g (=1.50 mol) of $C_{12}/C_{14}$-alcohol were placed in a heatable stirred vessel. After heating to about 60° C., 100 g (=1.00 mol) of succinic anhydride flakes (SA) were added over a period of about 15 minutes while stirring. Subsequently, the mixture was heated to 100° C. over ½ hour. An exothermic reaction occurred and the reaction mixture heated up to about 115° C. Stirring was continued for 3 hours at 90° C. and the acid number was subsequently checked. An acid number of 140 [mg KOH/g] was found.

Step 2 (Ca Salt Formation)

37.0 g of calcium hydroxide powder (=0.50 mol of $Ca(OH)_2$) and 74 g of water were added at 90° C. to the acidic monoester from step 1 over a period of 20–30 minutes. A slightly exothermic reaction could be detected. Stirring was then continued for 2 hours at 85–90° C. This gave 410 g of a white, viscous suspension which still flows at 35° C. The alkali number is determined by potentiometric titration with $HClO_4$ in glacialacetic acid. An alkali number of 130 [mg KOH/g] was found.

Step 3 (Partial Neutralization)

In this example, the partial neutralization was carried out in the actual ethoxylation reactor. For this purpose, 194 g of $C_{12}/C_{14}$-alcohol (=1.00 mol) as raw material to be ethoxylated were placed in the ethoxylation reactor and 2.05 g of the abovementioned precursor (from step 2) were added. This amount corresponded to 0.25 mol % of Ca, based on the fatty alcohol to be ethoxylated. This mixture was partially neutralized in the reactor using 0.24 g of $H_2SO_4$ (40% strength).

Step 4

The product from step 3 was dried at 90° C. under reduced pressure to remove water to a residual water content of $\leq 0.10\%$.

EXAMPLE A3

Step 1 (Ester Formation)

The procedure of Example A 1 was repeated, but 744 g (=2.00 mol) of $C_{12}/C_{14}$-alcohol ethoxylate containing 4 EO/mol were used in place of the $C_{12}/C_{14}$-alcohol. After step 1, an acid number of 66 [mg KOH/g] was found.

Step 2 (Ca Salt Formation)

The Ca salt formation was carried out as in Example A 1. This gave 410 g of a white, viscous suspension which still flows at 35° C. The determination of the alkali number gave a value of 63 [mg KOH/g].

Step 3 (Partial Neutralization)

The partial neutralization is carried out by a method analogous to Example A 1 using 49 g of 40% strength sulfuric acid at 60° C. This amount corresponds to 40% neutralization of the Ca basicity present.

Step 4 (Drying)

Drying is carried out by a method analogous to Example A 1. The substrate obtained is liquid at 20° C. and is a good catalyst for the ethoxylation of fatty alcohols.

EXAMPLE A4

Step (Ester Formation)

The procedure of Example A 1 was repeated, but replacing the $C_{12}/C_{14}$-alcohol by 1176 g (=6.00 mol) of $C_{12}/C_{14}$-alcohol. After step 1, an acid number of 44 [mg KOH/g] was found.

Step 2 (Ca Salt Formation)

The Ca salt formation was carried out as in Example A 1. This gave a white suspension which had a medium viscosity at 25° C. The determination of the alkali number gave a value of 43 [mg KOH/g].

Step 3 (Partial Neutralization)

49.0 g of 50% strength sulfuric acid were added at 60° C. to the basic Ca salt of the $C_{12}/C_{14}$-alcohol monoester of succinic acid from step 2 while stirring. This amount corresponds to 50% neutralization of the Ca basicity present.

Step 4 (Drying)

Drying is carried out by a method analogous to Example A 1. The substrate obtained is liquid at 20° C. and can be used as a catalyst for the preparation of fatty alcohol ethoxylates.

EXAMPLE A5

Preparation of a Ca-containing Catalyst Based on a Fluoroalcohol

Step 1 (Ester Formation)

1350 g (=3.00 mol) of a perfluoroalkylethanol homologue mixture of the empirical formula $F—(CF_2)_n—(CH_2)_m—OH$ (mixture of n=6 to 16, m=2) were placed in a heatable stirred vessel. After heating to about 60° C., 100 g (=1.00 mol) of succinic anhydride flakes (SA) were added over a period of about 15 minutes while stirring. Subsequently, the mixture was heated further to 90° C. over ½ hour. A slightly exothermic reaction occurred and the reaction mixture heated up to about 110–115° C. Stirring was then continued for 2 hours at 100° C. and the acid number was subsequently checked (sample dissolved in IPA/water, potentiometric titration with NaOH). An acid number of 39 [mg KOH/g] was found.

Step 2 (Ca Salt Formation)

37.0 g of calcium hydroxide powder (=0.50 mol of $Ca(OH)_2$) together with the same weight of water were then added at 80° C. over a period of 20–30 minutes. A slightly exothermic reaction is observed. The mixture was subsequently stirred further for 2 hours at 90–95° C. to form the Ca salt. This gave a white, viscous suspension which still flows at 25° C. The alkali number is determined by potentiometric titration with $HClO_4$ in glacialacetic acid. An alkali number of 37 [mg KOH/g] was found.

Step 3 (Partial Neutralization)

For the partial neutralization, 49 g of 40% strength sulfuric acid were added to the basic Ca salt of the perfluoroalkylethanol monoester of succinic acid from step 2. This amount corresponds to 40% neutralization of the Ca basicity present. The product was then dried at 75° C. under reduced pressure to remove the remaining amounts of water.

SUMMARY OF THE CATALYST PREPARATION EXAMPLES

| Example | | Molar ratio of alcohol:SA:Ca | Partial neutralization with $H_2SO_4$ x% of the Ca basicity |
|---|---|---|---|
| A 1 | Ca salt of the $C_{12}/C_{14}$-alcohol monoester of succinic acid | 3:1:0.5 | 40% |
| A 2 | Ca salt of the $C_{12}/C_{14}$-alcohol monoester of succinic acid | 1.5:1:0.5 | 40% in the ethoxylation reactor |
| A 3 | Ca salt of the $C_{12}/C_{14}$-alcohol + 4 EO monoester of succinic acid | 2:1:0.5 | 40% |
| A 4 | Ca salt of the $C_{12}/C_{16}$-alcohol monoester of succinic acid | 6:1:0.5 | 50% |
| A 5 | Ca salt of the perfluoroalkyl-ethanol monoester of succinic acid | 3:1:0.5 | 40% |

Examples of the use of the catalysts of the invention for ethoxylation

EXAMPLE E1

Variant a 194 g of $C_{12/14}$-alcohol (=1.00 mol) and 3.6 g of catalyst type A 1 (=0.25 mol % of Ca) were weighed into a glass pressure reactor and, after repeated flushing of the reaction chamber with nitrogen, were heated to 160° C. At this temperature, the metering-in of ethylene oxide was commenced. After an induction phase of about 15 minutes, the reaction of the ethylene oxide commenced, so that a total of 176 g of ethylene oxide (=4 mol of EO/mol) were reacted at 160–170° C. over about 2 hours.

EXAMPLE E2

Variant b

In this variant, the partial neutralization step is carried out in the ethoxylation reactor, as has already been described in Example A2: For this purpose, 194 g of $C_{12}/C_{14}$-alcohol (=1.00 mol) as raw material to be ethoxylated were placed in the ethoxylation reactor and 2.05 g of the abovementioned precursor (from Example A2, step 2) were added. This amount corresponds to 0.25 mol % of Ca, based on the fatty alcohol to be ethoxylated.

The resulting mixture was partially neutralized in the ethoxylation reactor using 0.24 g of $H_2SO_4$ (40% strength). The product was subsequently dried at 90° C. under reduced pressure to remove water to a residual water content of $\leq 0.10\%$.

The material was subsequently heated to 1 60° C. and the metering-in of ethylene oxide was commenced. After an induction phase of about 15 minutes, a total of 176 g of ethylene oxide (=4 mol of EO/mol) were metered in at 160–170° C. over about 2 hours.

These Examples E 1 and E 2 and also the Examples E 3 to E 9 according to the invention which were carried out in an analogous way are summarized in the following table. In addition, this table shows the Comparative Examples C 1 to C 4.

TABULATION OF THE ETHOXYLATION EXAMPLES

| Example | Starting material (1.00 mol in each case) | Catalyst type | Amount of catalyst | corresponds to mol % of Ca, based on mol of starting material | Mol of EO/mol of starting material | Hazen color number in accordance with DIN/ISO | Q index |
|---|---|---|---|---|---|---|---|
| E 1 | 194 g of $C_{12}/C_{14}$-alcohol | A 1 | 3.6 g | 0.25 mol % | 4 | 40 | 1970 |
| E 2 | 194 g of $C_{12}/C_{14}$-alcohol | A 2/Step 2 | 2.05 g | 0.25 mol % | 7 | 40 | 3240 |
| E 3 | 194 g of $C_{12}/C_{14}$-alcohol | A 4 | 6.5 g | 0.25 mol % | 10 | 30 | 3250 |

-continued

| Example | Starting material (1.00 mol in each case) | Catalyst type | Amount of catalyst | corresponds to mol % of Ca, based on mol of starting material | Mol of EO/mol of starting material | Hazen color number in accordance with DIN/ISO | Q index |
|---|---|---|---|---|---|---|---|
| E 4 | 267 g of unsaturated $C_{16}/C_{18}$-alcohol | A 2/Step 4 | 3 g | 0.37 mol % | 5 | 100 | 2400 |
| E 5 | 173 g of n/iso-$C_{11}$-alcohol (n:iso = 1:1) | A 3 | 4.5 g | 0.25 mol % | 5 | 50 | 1600 |
| E 6 | 212 g of methyl laurate | A 3 | 10.8 g | 0.6 mol % | 5 | 140 | 1130 |
| E 7 | 283 g of methyl $C_{16}/C_{18}$-carboxylate | A 1 | 29 g | 2 mol % | 50 | 200 | |
| E 8 | 450 g of perfluoroalkylethanol | A 5 | 20.8 g | 0.7 mol % | 5.5 | 70 | 4000 |
| E 9 | 450 g of perfluoroalkylethanol | A 5 | 20.8 g | 0.7 mol % | 11 | 60 | 4900 |
| C 1 | 194 g of $C_{12}/C_{14}$-alcohol | Catalyst No. 2 from EP-337239 | 1.9 g | 0.40 mol % Ca | 4 | 90 | 900 |
| C 2 | 194 g of $C_{12}/C_{14}$-alcohol | Catalyst No. 11 B from US 5600020 | 1.75 g | 0.16 mol % | 4 | 130 | 1850 |
| C 3 | 464 g of perfluoroalkylethanol | Catalyst D from EP 0516017 | 2.0 g of $SbCl_5$-Lewis base complex | 0.50 mol % $SbCl_5$ | 4.5 | 60 | 1230 |
| C 4 | 212 g of methyl laurate | Sodium methoxide | 8.8 g of 30% strength $NaOCH_3$ solution | 5.0 mol % | 5 | 400 | 60 |

The Q index is a measure of the homologue distribution. $Q = n \cdot p^2$, where n is the average adduct number (mean degree of ethoxylation) and p is the percentage of the adduct having the particular degree of ethoxylation which is present in the greatest amount. A high Q value thus indicates a narrow homologue distribution.

What is claimed is:

1. An alkoxylation catalyst prepared by
   a) reaction of one mol of a dicarboxylic acid of the formula $$HOOC-(CH_2)_a-COOH,$$

where a is from 1 to 4, with from 1.5 to 8 mol of an alcohol of the formula $$R-(OA)_x-OH$$

where R is $C_4$–$C_{22}$-alkyl, $C_4$–$C_{22}$-alkenyl or a group of the formula $F-(CF_2)_n-(CH_2)_m-$, n is an integer from 6 to 16, m is an integer from 1 to 4, x is a number from 0 to 6 and A is $-C_2H_4-$ or $-C_3H_6-$, to form the corresponding dicarboxylic monoester,
   b) formation of an alkaline earth metal salt of the dicarboxylic monoester by addition of water and from 0.45 to 0.55 mol of a basic alkaline earth metal compound per mol of dicarboxylic acid originally used,
   c) partial neutralization of the alkaline earth metal salt by addition of from 0.25 to 0.7 mol of $H_2SO_4$ per mol of basic alkaline earth metal compound originally used and
   d) removal of the water present at a temperature of less than 100° C.

2. A process for the alkoxylation of compounds containing an active H atom and also alkyl esters of fatty acids, wherein the alkoxylation is carried out in the presence of an alkoxylation catalyst as claimed in claim 1.

* * * * *